US008623363B2

(12) United States Patent
Burioni et al.

(10) Patent No.: US 8,623,363 B2
(45) Date of Patent: Jan. 7, 2014

(54) ANTI-HCV MONOCLONAL ANTIBODY AS A MEDICAMENT FOR THE THERAPEUTIC TREATMENT AND PREVENTION OF HCV INFECTIONS

(75) Inventors: Roberto Burioni, Rimini (IT); Massimo Clementi, Milan (IT)

(73) Assignee: Pomona Ricerca S.R.L., Turin (IT)

( * ) Notice: Subject to any disclaimer, the term of this patent is extended or adjusted under 35 U.S.C. 154(b) by 0 days.

(21) Appl. No.: 13/141,071

(22) PCT Filed: Dec. 21, 2009

(86) PCT No.: PCT/IB2009/055867
§ 371 (c)(1),
(2), (4) Date: Jun. 20, 2011

(87) PCT Pub. No.: WO2010/073204
PCT Pub. Date: Jul. 1, 2010

(65) Prior Publication Data
US 2011/0256140 A1 Oct. 20, 2011

(30) Foreign Application Priority Data

Dec. 22, 2008 (IT) ............................. T02008A0964

(51) Int. Cl.
*A61K 39/395* (2006.01)
(52) U.S. Cl.
USPC ..................................................... 424/141.1
(58) Field of Classification Search
None
See application file for complete search history.

(56) References Cited

U.S. PATENT DOCUMENTS

| | | | |
|---|---|---|---|
| 4,946,778 A | | 8/1990 | Ladner et al. |
| 5,245,015 A | * | 9/1993 | Fung et al. ............... 530/388.35 |
| 6,057,421 A | | 5/2000 | Muller et al. |
| 6,964,199 B2 | * | 11/2005 | Lee et al. ......................... 73/735 |
| 2003/0100741 A1 | | 5/2003 | Muller et al. |
| 2004/0224310 A1 | | 11/2004 | McGready |
| 2005/0080240 A1 | | 4/2005 | Kunert et al. |
| 2005/0221298 A1 | | 10/2005 | Muller et al. |
| 2008/0014205 A1 | | 1/2008 | Horowitz et al. |

FOREIGN PATENT DOCUMENTS

| | | |
|---|---|---|
| EP | 0675199 | 10/1995 |
| EP | 0621339 | 10/2004 |
| WO | 84/00687 | 3/1984 |
| WO | 92/15885 | 9/1992 |
| WO | 2011/117848 | 9/2001 |
| WO | 02/046235 | 6/2002 |
| WO | 02/055560 | 7/2002 |
| WO | 03/064473 | 8/2003 |
| WO | 2007/134327 | 11/2007 |
| WO | 2008/033159 | 3/2008 |
| WO | 2009/037297 | 3/2009 |
| WO | 2009/115972 | 9/2009 |
| WO | 2009/144667 | 12/2009 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Rudikoff et al (Proc. Natl. Acad. Sci. USA 1982 vol. 79: p. 1979-1983).*
MacCallum et al. (J. Mol. Biol. Oct. 11, 1996; 262 (5): 732-745).*
Holm et al. (Mol. Immunol. Feb. 2007; 44 (6): 1075-1084).*
Eren et al (J Virol, 80:2654-64, 2006).*
Levy et al (Hepat., 43:581-591, 2006).*
Braibant, M., et al. Antibodies to conserved epitopes of the HIV-1 envelope in sera from long-term non-progressors: prevalence and association with neutralizing activity, AIDS, 2006, 20: 1923-1930.
Bugli, F., et al., Mapping B-Cell Epitopes of Hepatitis C Virus E2 Glycoprotein Using Human Monoclonal Antibodies from Phage Display Libraries, Journal of Virology, Oct. 2001, 75: 9986-9990.
Ward S., et al., Binding activities of a repertoire of single immunoglobulin variable domains secreted from *Escherichia coli*, Nature, 1989, 341: 644-646.
Pantophlet, et al., "GP120: Target for Neutralizing HIV-1 Antibodies", Annual Review Immunology 2006, 24: 739-769.
Buironi, R., et al., Dissection of human humoral immune response against hepatitis C virus E2 glycoprotein by repertoire cloning and generation of recombinant fab fragments, Hepatology, 1998, 28: 810-814.
McMichael, J., HIV Vaccines, Annual Review of Immunology, 2006, 24: 227-255.
Buironi, R., et al., A Vector for the Expression of Recombinant Monoclonal Fab Fragments in Bacteria, Journal of Immunological Methods 1998, 217: 195-199.
Buironi, R. I Treponemi Intestinali Umani, Doctoral Thesis 1993, 1-156.
Baca, M., et al., Antibody Humanization Using Monovalent Phage Display, Journal of Biological Chemistry 1997, 272: 10678-10874.
Carter, P., et al., Humanization of an Anti-p185her2 Antibody for Human Cancer Therapy, PNAS 1992, 89: 4285-4289.
Cole, S., et al., A Strategy for the Production of Human Monoclonal Antibodies Reactive with Lung Tumor Cell Lines, Cancer Research 1984, 44: 2750-2753.
Molinari, N., et al., The Annual Impact of Seasonal Influenza in the US: Measuring Disease Burden and Costs, Vaccine 2007, 25: 5086-5096.
Rangel-Moreno, J., et al., B Cells Promote Resistance to Heterosubtypic Strains of Influenza via Multiple Mechanisms, The Journal of Immunology 2008, 180: 454-463.

(Continued)

*Primary Examiner* — Brad Duffy
(74) *Attorney, Agent, or Firm* — Steinfl & Bruno LLP

(57) ABSTRACT

The present invention relates to the monoclonal antibody e20 or a functional fragment thereof as a medicament for the therapeutic treatment and prevention of HCV infections. The e20 antibody is able to bind all of the known HCV genotypes and exhibits a strong neutralising activity against the virus, in particular towards genotypes 1a, 1b, 2a, and 4. A pharmaceutical composition is also described for the treatment or prevention of HCV infections, which comprises the monoclonal antibody e20 or a functional fragment thereof, and pharmaceutically acceptable excipients, carriers or diluents.

5 Claims, 3 Drawing Sheets

(56) References Cited

OTHER PUBLICATIONS

Figure 1:
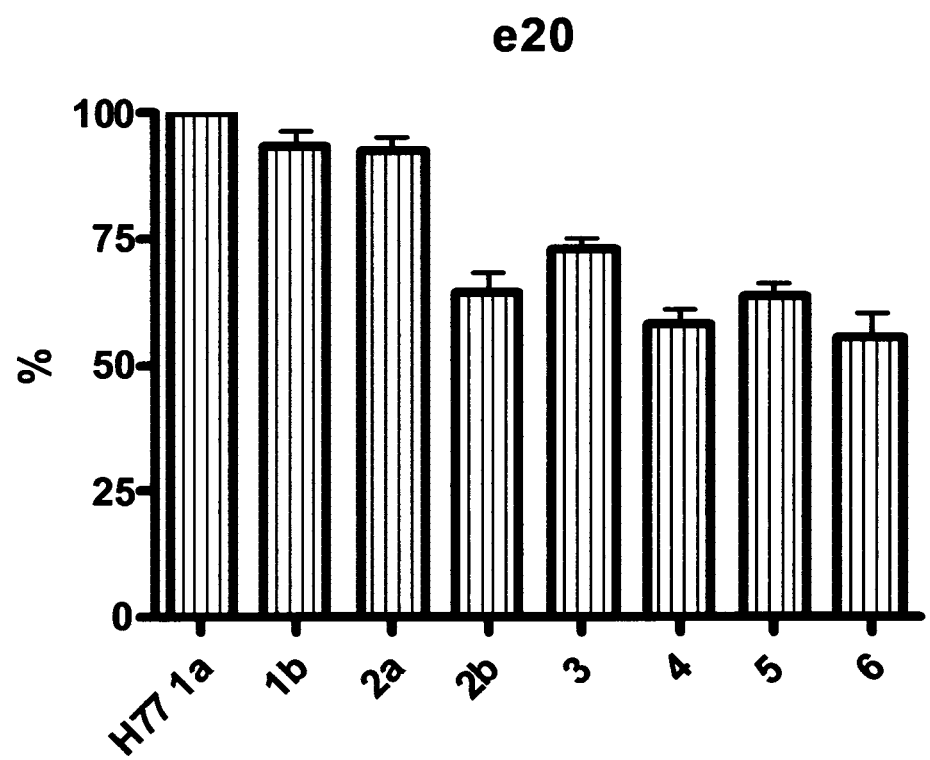

Thompson, W., et al., Mortality Associated with Influenza and Respiratory Syncytial Virus in the United States, JAMA 2003, 289: 179-186.
Austin, F., et al., Antigenic mapping of an Avian H1 Influenza virus haemagglutinin and interrelationships of H1 virus from humans, pigs and birds, Journal Gen. Virol. 1986, 67: 983-992.
Asanuma, H., et al., Influenza PR8 HA-specific fab fragments produced by phage display methods, Biochemical and Biophysical Research Communication 2008, 366: 445-449.
Tkacova, M., et al., Evaluation of monoclonal antibodies for subtyping of currently circulating human type A viruses, Journal of Clinical Microbiology 1997, 35: 1196-1198.
Burioni, R., et al., Dissection of human humoral immune response against Hepatitis C virus E2 glycoprotein by repertoire cloning and generation of recombinant fab fragments, Hepatology 1998, 28: 810-814.
Barbass, C., et al., Human primers for fab amplification: Original set, Phage Display Manual, 2004, CSH Press, A1.6-A1.7.
Smirnov, Y. et al., "An epitope shared by the hemagglutinins of H1, H2, H5, and H6 subtypes of influenza A virus." *Acta Virologica* 43(4):237-244 (1999).
Smirnov, Y. et al., "Prevention and treatment of bronchopneumonia in mice caused by mouse-adapted variant of avian H5N2 influenza a virus using a monoclonal antibody against conserved epitope in the HA stem region." *Archives of Virology* 145(8):1733-1741 (2000).
Throsby, M. et al., "Heterosubtypic neutralizing monoclonal antibodies cross-protective against H5N1 and H1N1 recovered from human IgM+ memory B cells." *PLOS One* 3(12):1-15 (2008).
Ziegler, T. et al., "Type- and subtype-specific detection of influenza viruses in clinical specimens by rapid culture assay." *Journal of Clinical Microbiology* 33(2):318-321 (1995).
Nguyen, HH., et al., Heterosubtypic Immunity to Influenza A Virus Infection Requires B Cells but not CD8+ Cytotoxic T Lymphocytes, The Journal of Infectious Diseases 2001, 183: 368-376.
Muller S. et al. "Generation and specificity of monoclonal anti-idiotypic antibodies against human HIV-specific antibodies," Journal of Immunology, vol. 147, No. 3, p. 933-941 (1991).
Wang, Haitao et al. "Human monoclonal and polyclonal anti-human immunodeficiency virus-1 antibodies share a common clonotypic specificity," *Eur. J. Immunol.* 1992, 22:1749-1755 (1992).
Humbert, Michael et al. "Mimotopes selected with antibodies from HIV-1-neutralizing long-term nonprogressor plasma," *Eur. J. Immunol.* 2007, 37:501-515.
Grant, Michael et al. "The anti-idiotypic antibody 1F7 selectively inhibits cytotoxic T cells activated in HIV-1 infection," *Immunology and Cell Biology*, 78, 20-27 (2000).
Muller S. et al. "Stimulation of Antiviral Antibody Response in SHIV-IIIb-Infected Macaques," *Scand. J. Immunol.*, 54, 383-395 (2001.
Muller S. et al. "Stimulation of HIV-1-neutralizing antibodies in simian HIV-IIIB-infected macaques," *Proc. Natl. Acad. Sci. USA*, vol. 95 pp. 276-281 (1998).
Wang, Q.L. et al. "Identification of an Idiotypic Peptide Recognized by Autoantibodies in Human Immunodeficiency Virus-1-infected Individuals," *The American Society for Clinical Investigation, Inc.*, vol. 96, 775-780 (1995).
Boudet, Florence et al. "Anti-Idiotypic Antibodies to the Third Variable Domain of gp120 Induce an Anti-HIV-1 Antibody Response in Mice," *Virology* 200, 176-188 (1994).
Kunert, Renate et al. "Molecular Characterization of Five Neutralizing Anti-HIV Type 1 Antibodies: Identification of Nonconventional D Segments in the Human Monoclonal Antibodies 2G12 and 2F5," *AIDS Research and Human Retroviruses*, vol. 14, No. 13, pp. 1115-1128 (1998).
Kasai, Yasushi et al. "Molecular cloning of murine monoclonal anti-idiotypic Fab," *Journal of Immunological Methods*, 155, 77-89 (1992).
Burton, Human primers for fab amplification: original set, Phage Display Manual, A1.6-A1.7.
Müller, S., et al., Generation and specificity of monoclonal anti-idiotypic antibodies against human HIV-specific antibodies, The Journal of Immunology 1991, 147: 933-941.
Perotti, M., et al., Identification of a broadly cross-reacting and neutralizing human monoclonal antibody directed against the Hepatitis C virus E2 protein, Journal of Virology 2008, 82: 1047-1052.
Hariharan, K., et al., Analysis of the cross-reactive Anti-gp120 antibody population in human immunodeficiency virus-infected asymptomatic individuals, Journal of Virology, 1993, 67: 953-960.
Sui, Jianhua et al., "Structural and functional bases for broad-spectrum neutralization of avian and human influenza A viruses", Nature Structural and Molecular Biology 2009, 16: 265-27.
PCT International Search Report issued for PCT Application No. PCT/IB2010/052434 filed on Jun. 1, 2010 in the name of Pomona Biotechnologies Inc.
PCT Written Opinion issued for PCT Application No. PCT/IB2010/052434 filed on Jun. 1, 2010 in the name of Pomona Biotechnologies Inc.
PCT International Search Report issued for PCT Application No. PCT/IB2008/050307 filed on Jan. 29, 2008 in the name of Pomona Biotechnologies Inc.
PCT Written Opinion issued for PCT Application No. PCT/IB2008/050307 filed on Jan. 29, 2008 in the name of Pomona Biotechnologies Inc.
PCT International Search Report issued for PCT Application No. PCT/IB2009/052212 filed on May 27, 2008 in the name of Pomona Biotechnologies Inc.
PCT Written Opinion issued for PCT Application No. PCT/IB2009/052212 filed on May 27, 2008 in the name of Pomona Biotechnologies Inc.
PCT International Search Report issued for PCT Application No. PCT/IB2009/051068 filed on Mar. 16, 2009 in the name of Pomona Biotechnologies Inc.
PCT Written Opinion issued for PCT Application No. PCT/IB2009/051068 filed on Mar. 16, 2009 in the name of Pomona Biotechnologies Inc.
Non-Final Office Action issued for U.S. Appl. No. 12/524,816, filed Jul. 28, 2009 in the name of Roberto Burioni et al. mail date: Jul. 21, 2011.
Restriction Requirement issued for U.S. Appl. No. 12/524,816, filed Jul. 28, 2009 in the name of Roberto Burioni et al. mail date: Apr. 5, 2011.
Chen, C., et aI., Enhancement and destruction of antibody function by somatic mutation: unequal occurence is controlled by V gene combinatorial associations, EMBO J. 1995, 14(12):2784-2794.
Winkler, K., et aI., Changing the antigen binding specificity by single point mutations of an anti-p24 (HIV-1) antibody, J. Immunol. 2000, 165:4505-4514.
Bansal, G. P., A summary of the workshop on passive immunization using monoclonal antibodies for HIV/AIDS, held at the National Institute of Allergy and Infectious Diseases, Bethesda, Mar. 10, 2006, BioI. 2007, 35:367-371.
Trkola, A., et aI., Delay of HIV-1 rebound after cessation of antiretroviral therapy through passive transfer of human neutralizing antibodies, Nat. Med. 2005, 11 (6):615-622.
Montefiori, D. C., Neutralizing antibodies take a swipe at HIV in vivo, Nat. Med. 2005, 11 (6):593-594.
Haigwood, N. L., Predictive value of primate models for AIDS, AIDS Rev. 2004, 6:187-198.
Staprans, S. I., and M. B. Feinberg, The roles of nonhuman primates in the clinical evaluation of candidate AIDS vaccines, Exp. Rev. Vacc. 2004, 3(4):S5-S32.
PCT International Search Report for PCT/IB2009/055867 filed Dec. 21, 2009 in the name of Bait Biotecnologie Applicate Italiane S.R.L.
PCT Written Opinion for PCT/IB2009/055867 filed Dec. 21, 2009 in the name of Bait Biotecnologie Applicate Italiane S.R.L.
PCT International Search Report for PCT/IT2003/000032 (WO 03/064473) filed Jan. 29, 2003 in the name of Roberto Burioni.
PCT International Search Report for PCT/US2001/045221 (WO 02/055560) filed Nov. 30, 2001 in the name of the Gouvernment of the United States of America, as represented by the Secretary Department of Health and Human Services.

(56) References Cited

OTHER PUBLICATIONS

D. X. Johansson et al., "Human combinatorial libraries yield rare antibodies that broadly neutralize hepatitis C virus", PNAS, vol. 104; No. 41; 16269-16274 (2007).

R. Burioni, "Nonneutralizing Human Antibody Fragment against Hepatitis C Virus E2 Glycoprotein Modulate Neutralization of Binding Activity of Human Recombinant Fabs", Virology, vol. 288; No. 1; 29-35 (2001).

A. Tarr et al., "Characterization of the Hepatitis C Virus E2 Epitope Defined by the Broadly Neutralizing Monoclonal Antibody AP33", Hepatology, vol. 43; No. 3; 592-601 (2006).

Burioni, R., et al., Molecular cloning of the first human monoclonal antibodies neutralizing with high potency Swine-origin Influenza A pandemic virus (S-OIV), New Microbiologica 2009, 32: 319-324.

Burton, D., Antibodies, viruses and vaccines, Nature 2002, 2: 706-713.

Padaln, E.A., et al., Identification of specificity-determing residues in antibodies, The FASED Journal 1995, 9: 133-1139.

Prophylactic, Webster dictionary definition 2005.

Knight, Dm et al., Stable expression of cloned human antibody genes in murine myeloma cells, Hum Antibodies Hydridomas 1992, abstract only.

Li, B et al., Preparation of Anti-Idiotypic Antibody against Avian Influenza Virus Subtype H9, Ceelular & Moelcular Immunology 2005, 2: 155-157.

Notice of Allowance mailed on Oct. 4, 2012 issued for U.S. Appl. No. 12/524,816, filed Jul. 28, 2009 in the name of Roberto Burioni et al.

Final Office Action mailed on May 9, 2012 issued for U.S. Appl. No. 12/524,816, filed Jul. 28, 2009 in the name of Roberto Burioni et al.

Restriction Requirement mailed on Sep. 7, 2012 issued for U.S. Appl. No. 12/922,850, filed Sep. 15, 2010 in the name of Roberto Burioni et al.

Non-Final Office Action mailed on Dec. 5, 2012 issued for U.S. Appl. 12/994,746, filed Nov. 24, 2010 in the name of Roberto Burioni et al.

Restriction Requirement mailed on Aug. 28, 2012 issued for U.S. Appl. No. 13/265,542, filed Oct. 20, 2011 in the name of Roberto Burioni et al.

Non-Final Office Action mailed on Oct. 25, 2012 issued for U.S. Appl. No. 13/265,542, filed Oct. 20, 2011 in the name of Roberto Burioni et al.

Notice of Allowance mailed on Mar. 22, 2013 issued for U.S. Appl. No. 13/265,542, filed Oct. 20, 2011 in the name of Roberto Burioni et al.

Ribavirin—antiviral Product Specification, Sigma-Aldrich, 1 page.

Merriam-Webster, Definition of disparage, www.merriam-webster.com/dictionary/disparage, retrieved May 17, 2013, 3 pages.

Matsuura, Y. et al., Characterization of Pseudotype VSV Possessing HCV Envelope Proteins, Virology 2001, 286: 263-275.

Rosa, D. et al., A quantitative test to estimate neutralizing antibodies to the hepatitis C virus: Cytofluorimetric asSessment of envelope glycoprotein 2 binding to target cells, Proc. Natl. Acad. Sci. USA 1996, vol. 93: 1759-1763.

* cited by examiner

ANTI-HCV MONOCLONAL ANTIBODY AS A MEDICAMENT FOR THE THERAPEUTIC TREATMENT AND PREVENTION OF HCV INFECTIONS

CROSS REFERENCE TO RELATED APPLICATIONS

The present application is the US national stage of International Application PCT/IB2009/055867 filed on Dec. 21, 2009, which, in turn, claims priority to Italian Patent Application TO2008A000964 filed on Dec. 22, 2008.

The present invention relates to a monoclonal antibody against the Hepatitis C Virus (HCV) E2 glycoprotein as a medicament for the therapeutic treatment and prevention of HCV infections.

HCV is a virus having a pericapsid and a single stranded RNA, belonging to the Flavivirus family. Based on the genetic differences observed among the different HCV isolates, this virus species is categorized into 6 different genotypes, each of which is marked with a number. Each genotype, in turn, comprises a number of subtypes, each one of them is marked with a letter. The prevalence and distribution of the different HCV genotypes is variable throughout the world. In Europe, the predominant genotype is 1 b, whereas in North America, the genotype 1 a prevails. Determining the genotype is important from a clinical point of view, as such a feature contributes in determining the potential response to the therapy based on the combination of alpha interferon with ribavirin, which is currently the most used treatment. In fact, genotypes 1 and 4 are less responsive than genotypes 2, 3, 5 and 6 to the interferon-based therapy.

To date, no vaccines and no immunotherapies are available which proved to be really effective against Hepatitis C virus. The high variability of HCV's antigenic structure has so far hindered the development of antibodies capable of neutralising the virus, while being endowed with cross-reactivity towards the different virus genotypes. There is thus a need for anti-HCV antibodies that are provided with such features and accordingly are really effective in the therapy and prevention of HCV infections.

Antibodies directed against HCV are described in the prior art. For instance, Burioni et al., *Hepatology* Vol. 28, n. 3, 1998, describe the cloning and characterization of sequences encoding five recombinant human antibody fragments (Fab) specific for the HCV E2 glycoprotein (HCV E2), capable of binding to glycoproteins from different virus genotypes (cross-reactivity). Among the Fabs described in this article there is the antibody fragment designated as e20. Burioni et al., 1998, cit. describe that e20 has a high minimal activity in neutralising HCV E2 binding (NOB activity). However, in spite of the high NOB activity, in the International Patent Application WO 03/064473, the e20 antibody fragment is described as unable to neutralise viral infection even at high concentrations (80 µg/ml) (see, in particular, page 16, lines 8-10 in WO 03/064473).

The present inventors have now surprisingly found that, contrary to what stated in the prior art and in particular in WO 03/064473, the e20 fragment is capable of effectively neutralising the infection by different HCV genotypes in vitro. This makes e20 particularly suited for HCV neutralisation and elimination of HCV-infected cells and for use as a medicament for immunotherapy and immuno-prevention of HCV infections.

The attainment of such a result required a long and complex experimental work, which is illustrated in detail in the experimental section that follows.

In extreme synthesis, the experimental work carried out by the present inventors has allowed to demonstrate that the e20 antibody fragment exhibits the following unexpected features:

it is generated in the course of a natural infection due to an HCV strain belonging to genotype 1b, but is able to bind to the glycoproteins from all of the known HCV genotypes (particularly genotypes 1a, 1b, 2a, 2b, 3, 4, 5 and 6) and as such is largely cross-reactive;

it possesses a particularly high neutralisation ability towards HCV genotypes 1a, 1b, 2a and 4, as measured by a neutralisation assay based on HCV pseudo-particles (HCVpp);

certain amino acid residues essential for the binding of e20 to HCV E2 glycoprotein are also essential in HCV infection, which suggests that mutants capable of escaping e20 binding are at the same time provided with a decreased replication ability.

The above-mentioned features are apparently advantageous to the end of using the e20 antibody fragment as a medicament for immunotherapy and immunoprevention of HCV infections.

A first object of the invention is thus a monoclonal antibody or a fragment thereof, capable of binding the HCV E2 glycoprotein from a plurality of different HCV genotypes, as a medicament for the therapeutic treatment or prevention of HCV infections, characterised in that the monoclonal antibody or fragment thereof comprises at least one heavy chain variable region comprising the amino acid sequence SEQ ID NO: 1 or a sequence at least 90% identical to SEQ ID NO: 1 and at least one light chain variable region comprising the amino acid sequence SEQ ID NO: 2 or a sequence at least 90% identical to SEQ ID NO: 2.

Further preferred sequence identity percentages are at least 91%, 92%, 93%, 94%, 95%, 96%, 97%, 98% or 99%, wherein the expression "at least" refers to each of the percentages listed.

In one embodiment of the invention, the heavy chain variable region is encoded by the nucleotide sequence SEQ ID NO: 3 and the light chain variable region is encoded by SEQ ID NO: 4.

The term "antibody" is intended to refer to any class of full-length immunoglobulins and any fragment thereof comprising a light chain variable region and a heavy chain variable region, such as for example a Fab, a F(ab')2, a CDR (Complementarity Determining Region), or a single chain antibody comprising both heavy and light chain variable regions or CDRs, or scaffolds comprising one or more copies of CDR fragments from immunoglobulin heavy and light chain variable regions. This includes functional antibody fragments designated as ScFvs, diabodies, VHHs or isolated light or heavy chains. The expression "antibody" further encompasses antibodies that can be generated by using the sequences of the e20 antibody fragment variable region in a shuffling process for the light chain variable region, in order to establish VH/VL combinations with improved affinity, stability and/or recombinant production properties. The expression "antibody" also includes any type of full-length immunoglobulin or immunoglobulin fragment fused to specific full-length immunoglobulins or immunoglobulin fragments, which can target the e20 antibody fragment or the immunoglobulin to specific tissues, cells or soluble protein structures. The monoclonal antibody of the invention is preferably human.

The antibody used in the invention may be in the free form or in a conjugated form. A conjugated form is an antibody, as defined above, conjugated with a molecule capable of modulating the in vivo persistency, promoting or limiting the body distribution, decreasing the sensitivity to proteolytic agents, decreasing antigenicity, increasing the cytotoxic ability and/or facilitating the detection in body fluids and tissues. Non-limiting examples of molecules suitable for conjugation include human serum albumin, maltose-binding protein, glutathione-S-transferase, phage coat p3 or p8 proteins, peptides, sugars, PEG or PEG-like molecules, animal-, plant- or microbiology-derived toxins, cytokines, enzymes, chemiluminescent compounds, bioluminescent compounds, metal atoms, radioisotopes, fluorescent compounds, tagging groups or substrates for phosphorylation, glycosylation, ubiquitination, SUMOylation or endoproteolytic cleavage. In order to facilitate the conjugation, the antibody C-terminus or N-terminus can be modified, for example, by inserting additional amino acid residues, for instance one or more cysteine residues that are able to form disulphide bridges. The antibody used in the invention can also be linked to human erythrocytes or other cell carriers, to specific formulations, or to sustained-release systems such as, but without limitation, liposomes, dendrimers, microsomes, nanoparticles, microcapsules, virus vectors and the like.

Another object of the invention is a pharmaceutical composition for the therapeutic treatment or prevention of HCV infections, comprising a pharmaceutically effective amount of a monoclonal antibody or fragment thereof as defined above.

The composition of the invention may be administered to a subject infected or at risk of being infected with HCV. Any suitable administration route may be employed, including parenteral, oral, ocular, topical, loco-regional, enema or aerosol administration. The parenteral administration includes intramuscular injection, intravenous injection, intralymphatic injection, subcutaneous or intradermic injection and infusion.

The composition of the invention may be prepared in any pharmaceutical form that is suitable for the selected administration route, for instance in the form of an injectable solution or suspension, an infusion, a tablet, a capsule, a cream, an ointment, a lotion, or a suppository.

The composition of the invention comprises the antibody or a fragment thereof, as defined above, as the active principle, as well as suitable pharmaceutical excipients, carriers or diluents known to the person of skill in the art.

A further object of the invention is an anti-idiotype antibody capable of specifically binding to the idiotype of the antibody or fragment thereof as defined above. The anti-idiotype antibody of the invention can be obtained by conventional methods for obtaining anti-idiotype antibodies, which are per se known to the person of skill in the art.

The invention is further described in detail in the following experimental section provided solely by way of illustration, by referring to the enclosed figures, wherein:

FIG. 1 shows the binding of e20 to HCV E2 glycoproteins from different genotypes. The data are displayed as the percentage of positive fluorescent cells.

Figure 2:
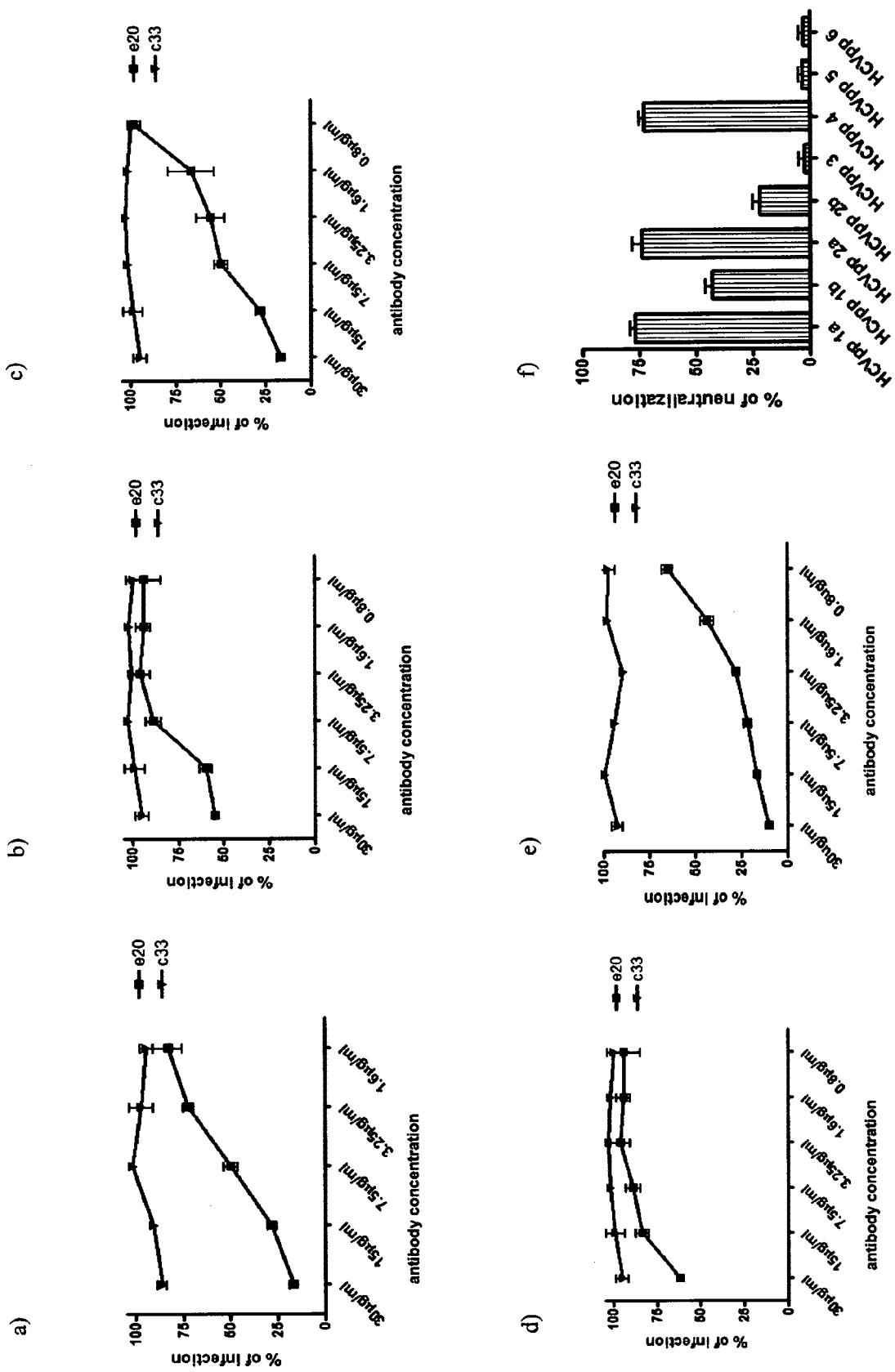

FIG. 2 shows the neutralising activity of Fab e20 by using virus pseudo-particles that exhibit E1-E2 glycoproteins from genotype 1 a: UKN1A20.8 (a); E1E2 genotype 1b: UKN1B5.23 (b); E1E2 genotype 2a: UKN2A1.2 (c); E1E2 genotype 2b: UKN2B1.1 (d); E1E2 genotype 4: UKN4.21.16 (e). (f) Neutralising activity of Fab e20 at 15 μg/ml by using virus pseudo-particles that exhibit E1-E2 from different genotypes (UKN1A20.8, UKN1B5.23, UKN2A1.2, UKN2B1.1; UKN3A13.6, UKN4.21.16, UKN5.15.11, UKN6.5.8).

Figure 3:
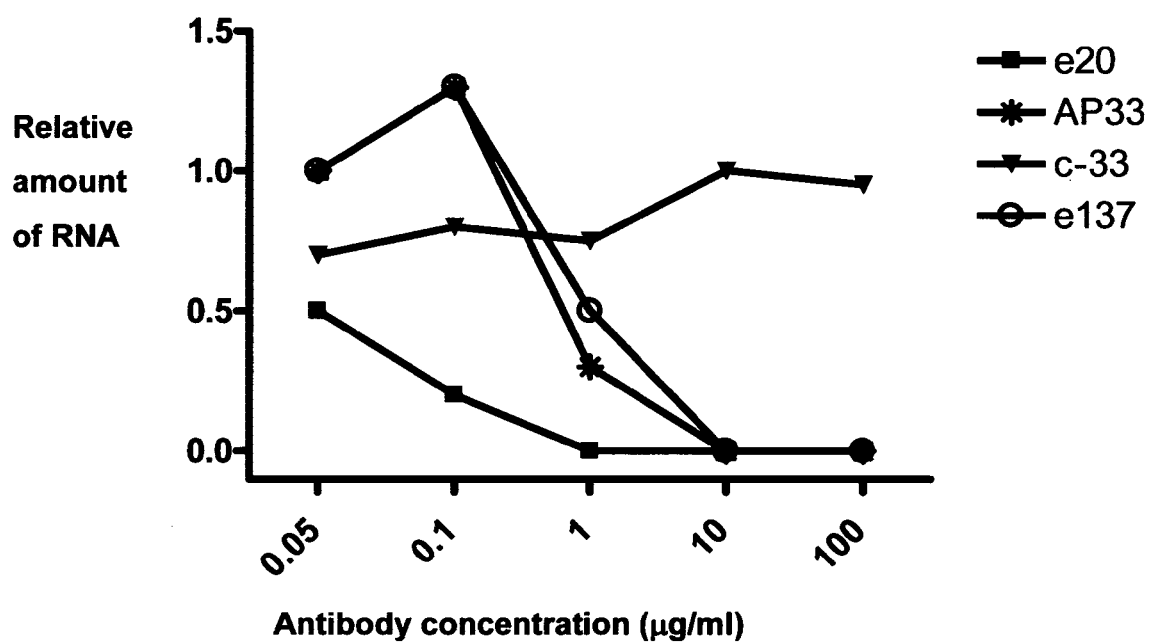

FIG. 3 shows the neutralising activity of e20 and other anti-HCV antibodies (e137, AP33) by using the HCVcc system (genotype 2a). JFH-1 infectivity in the presence of e20 and the negative control Fab (c33-3) is displayed as the amount of viral RNA normalised to glyceral-dehyde-3-phosphate dehydrogenase RNA, as determined by quantitative reverse transcription PCR.

EXPERIMENTAL SECTION

Cloning Strategy

The preparation of random combinatorial libraries displayed on surfaces of filamentous phages represents a highly potent tool for selecting high affinity human monoclonal antibodies. In fact, the selection procedure based on phage display is extremely versatile and can be optimised so as to select cross-reactive antibodies. In particular, e20 was cloned as an IgG1 Fab fragment from the lymphocyte B repertoire of a 58 year old woman who was persistently infected with an HCV strain belonging to genotype 1b. In order to select the cross-reactive clones, the library derived from the patient was subjected to panning against recombinant HCV E2 glycoprotein derived from a virus isolate belonging to a different genotype, that is 1a. Briefly, with this approach it has been possible to obtain antibodies that are generated in the course of a natural infection, yet are all the same able to bind to different glycoproteins never encountered by the immune system of the patient selected for the study.

Study of the Heavy and Light Chain Sequences

The sequencing of the e20 heavy and light chain genes and the study of their mutational pattern (Table 1) showed that this antibody is derived from a somatic mutation process, that is a process stimulated in an antibody clone by the continuous contact with the specific antigen, in order to improve the affinity of the antibody itself for the antigen.

As regards the heavy chain, e20 exhibits a nucleotide sequence homology to the germinal line gene below 85%. The mutational pattern shows a typical distribution for a somatically mutated clone, with a specific polarisation in the Complementarity Determining Regions (CDRs). The examination of the e20 joining region (that is the joining region that gives rise to CDR3) shows that this is made up of a V gene belonging to the VH1-69 subfamily (a highly represented gene in a human anti-HCV humoral response), a D gene belonging to the D2-21 subfamily, and a JH gene belonging to the JH4 subfamily.

In a similar way, the e20 light chain (isotype K) exhibits a mutation percentage consistent with a somatic mutation process, as shown by polarisation in the CDRs. The examination of the joining region reveals that the e20 light chain CDR3 arises from the κV joining of a KV gene belonging to the κV3-15 subfamily, and a κJ gene belonging to the κJ5 subfamily.

The sequence data allow for the conclusion that e20 is not an artificial antibody, but on the contrary is actually present in the antibody repertoire of the patient selected for the study.

TABLE 1 a)

| gene V | gene D | gene J | length of CDR 3 | % mutated nucleotides | | % mutated amino acids | | mutations R:S | |
|---|---|---|---|---|---|---|---|---|---|
| | | | | FR | CDR | FR | CDR | FR | CDR |
| V1-69 | D 2-21 | J 4 | 18 | 9.4 | 16.9 | 19 | 38 | 13:2 | 5:1 | b)

| gene V | gene J | length of CDR 3 | % mutated nucleotides | | % mutated amino acids | | mutations R:S | |
|---|---|---|---|---|---|---|---|---|
| | | | FRs | CDRs | FRs | CDRs | FRs | CDRs |
| KV 3-15 | KJ 5 | 9 | 1.5 | 10.4 | 1.5 | 11.5 | 1:2 | 3:5 |

The Table 1 hereinabove shows the mutational patterns for the germinal lines and the gene V in e20 heavy chain a) and light chain b). The amino acid and nucleotide mutation percentages were calculated according to the alignment method of Kabat and Wu, by taking into account FR1, FR2, and FR3 for the light and heavy chains, CDR1 and CDR2 for the heavy chains, and CDR1, CDR2, and CDR3 for the light chains. The ratio of replacement mutations (R) to silent mutations (S) is also reported.

Assessment of e20 Binding to E2 Derived from Different HCV Genotypes

The e20 fragment in the form of a Fab was tested for the ability to recognise the E2 glycoprotein from HCV genotypes other than 1b (i.e. the genotype of the strain that had infected the patient from whom e20 was obtained) and 1a (i.e. the genotype employed for cloning the Fab). The difficulties experienced in obtaining soluble E2 forms from different HCV geno-types required the use of an alternative FACS-based approach.

Briefly, 293T human epithelial kidney cells (HEK) were grown in Dulbecco's modified Eagle's medium (DMEM), supplemented with 10% fetal calf serum, 5% non-essential amino acids, 200 mM glutamine, streptomycin (100 μg/ml) and penicillin (100 U/ml). Once 80% confluence was reached, 2×10⁶ HEK cells were seeded in 10 cm plates and 24 hours later were transfected with 3 μg of phCMV-7, an expression vector encoding for the E1E2 glycoproteins from different HCV genotypes, by using a calcium phosphate transfection protocol. The medium was replaced 16 hours after the transfection and the cells were then incubated at 37° C. for 24 hours. The medium was discarded and the cell monolayer was washed twice with PBS. 5 ml of dissociation buffer were added and the cells were incubated at 37° C. for 5 minutes. The cells were washed twice with PBS and centrifuged at 1000 rpm for 5 minutes; 1.2 ml of fixing reagent were added to the pellet obtained from each plate. The cells were incubated for 15 minutes at room temperature. The samples were washed in 5 ml of PBS supplemented with 2% fetal calf serum (FPBS), then centrifuged at 1000 rpm for 5 minutes of Fab e20 at a final 100 μl of permeabilising reagent were added to the pellet with 50 μl concentration of 10 μg/ml. A similar protocol was also followed for non-transfected cells, used as a control. After a 40-minute incubation at room temperature, the samples were washed in 5 ml of FPBS and 50 μl of FITC-conjugated secondary antibody were added to the pellet. The cells were incubated for 20 minutes at room temperature and were washed twice in 5 ml of FPBS. Finally, the supernatant was removed, the pellet was resuspended in 300 μl of FPBS, and the cells were analysed by FACS. The binding activity was expressed as the percentage of positive fluorescent cells obtained from the percentage of cells having a higher fluorescence level than cells without Fab e20. A recombinant human Fab (c33-3) specific for a non-structural HCV antigen (NS3) was included as a negative control in each experiment.

This approach showed that Fab e20 was capable of recognising all of the expressed HCV E2 genotypes (1a; 1b; 2a; 2b; 3; 4; 5; 6), with a higher percentage of fluorescent cells than that obtained with the control Fab. The results are shown in FIG. 1.

Assessment of e20 Binding to E2 Glycoproteins from HCV 1a Mutated within CD81-Binding Regions Fab e20 was also tested against a panel of E1 E2 derived from H77 (genotype 1a) mutated within conserved regions, described as being crucial for CD81 binding and for the infectivity of HCV pseudo-particles (HCVpp). Each conserved location in this region was mutated in alanine. All these substitutions resulted in loss of infectivity in the HCVpp assay described below. Binding of the Fab e20 HCV E2 glycoprotein is abrogated by some of these crucial mutations (Table 2).

The data described in Table 2 suggest that e20 binds to an E2 region essential for virus infection. These data also confirm that e20 binds to a region critical for AP33 binding, the neutralising anti-HCV antibody with the largest cross-reactivity, but less suitable as a template for the design of a vaccine medicament and for use in immunotherapy, taking into consideration that immunotherapy with heterologous antibodies is not feasible and that the presence of similar antibodies in the human repertoire is extremely rare (Tarr et al. *J Gen Virol*. 88:2991. 2007). Still more interestingly, this analysis clearly showed that all of the mutants not recognised by e20 do not allow for the infection of target cells in a pseudo-virus model.

TABLE 2

| | Q412A | I413A | T414A | N415A | T416A | N417A | G418A | S419A | W420A | H421A | I422A | N423A | R483A |
|---|---|---|---|---|---|---|---|---|---|---|---|---|---|
| e20 binding activity | 100 | 100 | 95 | 98 | 96 | 97 | 100 | 100 | 97 | 100 | 100 | 100 | 100 |
| HCVpp infectivity | 5 | 0 | 0 | 0 | 0 | 12 | 0 | 100 | 0 | 0 | 0 | 0 | 0 |

| | P484A | Y486A | W487A | H488A | Y527A | W529A | G530A | N532A | D533A | T534A | D535A | N540A | R543A |
|---|---|---|---|---|---|---|---|---|---|---|---|---|---|
| e20 binding activity | 100 | 95 | 100 | 100 | 92 | 0 | 3 | 100 | 100 | 100 | 10 | 70 | 68 |
| HCVpp infectivity | 100 | 5 | 0 | 0 | 5 | 0 | 0 | 25 | 30 | 25 | 0 | 40 | 0 |

| | P544A | P545A | G547A | W549A | F550A |
|---|---|---|---|---|---|
| e20 binding activity | 72 | 97 | 98 | 96 | 94 |
| HCVpp infectivity | 35 | 80 | 0 | 0 | 5 |

The hereinabove Table 2 shows e20 binding to E1 E2 derived from H77 mutants (genotype 1a). The binding activity is expressed as the percentage of that measured with the wild-type H77 protein.

Assessment of e20 Neutralising Activity on HCV Pseudo-Particles Derived from Different Genotypes Fab e20 neutralising activity was then verified in a neutralisation assay based on HCV pseudo-particles (HCVpp).

Briefly, 293T human epithelial kidney cells (HEK) and Huh-7 human hepatoma cells were grown in DMEM supplemented with 10% fetal calf serum, 5% non-essential amino acids, 200 mM glutamine, streptomycin (100 µg/ml) and penicillin (100 U/ml). Once 80% confluence was reached, $2 \times 10^6$ HEK cells were seeded in 10 cm plates and 24 hours later were co-transfected with 8 µg of mouse leukemia virus vector (MLV) Gag-Pol, 8 µg of MLV transfer vector encoding luciferase, and 3 µg of full-length phCMV-7a expression vector encoding for the E1 E2 glycoproteins from different HCV genotypes. One day later, the transfection medium was replaced with 5 ml of fresh medium containing 10 mM HEPES. The cells were incubated for 24 hours at 37° C. The target cells (Huh-7) were seeded in 24-well plates at $2.5 \times 10^4$ per well and incubated overnight at 37° C. The HCV pseudo-particles (HCVpp) were collected 24 hours after the replacement of the medium, centrifuged at 2000 rpm for 10 minutes and filtered through 0.45 µm pore-size membranes and used in a neutralisation assay.

In particular, 60 µl of HCVpp-containing medium were mixed with 90 µl of different concentrations of Fab e20 and incubated for 1 hour at 37° C. Such a mixture was added to the Huh-7 target cells and the cells were incubated for 3 hours at 37° C. Finally, the inoculation was removed, 1 ml of fresh medium was added to each well, and the cells were incubated at 37° C. for 4 days. The cells were washed twice with PBS and then lysed with 100 µl of lysis buffer (Promega), following the manufacturer's instructions. The cell lysate was transferred to 96-well plates and 100 µl of substrate/buffer (Promega) were added to each well. The infection of the cells was analysed by measuring the luminescence activity (Chameleon plate reader, Hidex), given in relative light units (RLUs). The neutralising activity was determined as the percentage of infection, by comparing the luminescence obtained to that detected in the HCVpp wells in the absence of antibodies capable of competition (neg). A recombinant human Fab (c33-3) specific for a non-structural HCV antigen (NS3) was included as a negative control in each experiment.

This approach showed that e20 is able to strongly neutralise HCV genotypes 1a and 4. E20 exhibits a 50% neutralising activity on genotype 1a at 7.5 gg/ml concentrations and a 75% inhibition on genotype 4 at 15 gg/ml (FIGS. 2a, 2e, and 2f). However, this antibody is also able to strongly neutralise HCV genotypes 1b and 2a. In more detail, at 15 gg/ml, e20 shows a 40% neutralisation and a 75% infectivity of genotypes 1b and 2a, respectively (FIGS. 2b, 2c, and 2f). Finally, e20 is capable of neutralising in a lower degree HCVpps having genotype-2b E1 E2 glycoproteins, showing a 20% inhibition at 15 gg/ml (FIGS. 2d and 2f).

e20 Neutralising Activity of an HCV Strain Grown in Cell Culture (Genotype 2a, Strain JFH1)

The neutralising activity of HCV e20 was also tested by using an HCVcc model system (HCV cell culture), by using a stable human hepatoma cell line containing a cDNA, integrated in a chromosome, from HCV genotype 2a (JFH1) and highly producing infective viruses (FIG. 3). Such a system allows for the assessment of the neutralising activity by using an infective hepatitis C virus strain. In this set of experiments, different concentrations of Fab e20 were incubated with the medium containing the virus generated in the HCVcc assay. After 3 hours, the mixture was added to target cells (Huh7.5). The infectivity was assessed by measuring the levels of the HCV positive strand RNA. Fab e20 showed a strong neutralising activity, as at a concentration of 1 µg/ml, which is very low, it is capable of abrogating completely the infectivity of HCV genotype 2a. Fab e20 neutralising activity is comparable to the mouse AP33 IgG monoclonal antibody, one of the strongest cross-neutralising antibodies described to date.

The invention claimed is:

1. A method for therapeutic treatment of HCV infections in a subject, the method comprising administering to the subject an effective amount of a monoclonal antibody or fragment thereof, capable of binding the HCV E2 glycoprotein from a plurality of different HCV genotypes, wherein the monoclonal antibody or fragment thereof comprises at least one heavy chain variable region comprising the amino acid sequence SEQ ID NO:1 and at least one light chain variable region comprising the amino acid sequence SEQ ID NO:2.

2. The method according claim 1 wherein the monoclonal antibody or fragment thereof is selected from a Fab, a F(ab')2, or a single chain antibody comprising both heavy and light chain variable regions.

3. The method according claim 1 wherein the monoclonal antibody or fragment thereof is in free form.

4. The method according claim 1 wherein the monoclonal antibody or fragment thereof is conjugated with a molecule capable of modulating the in vivo persistency, promoting or limiting the body distribution, decreasing the sensitivity to proteolytic agents, decreasing antigenicity, increasing the cytotoxic ability and/or facilitating the detection in body fluids and tissues.

5. The method according claim 1 wherein the monoclonal antibody or fragment thereof is fused with a specific full-length immunoglobulin or immunoglobulin fragment capable of targeting the antibody to specific tissues, cells or soluble protein structures.

* * * * *

SEQUENCE LISTING

<160> NUMBER OF SEQ ID NOS: 4

<210> SEQ ID NO 1
<211> LENGTH: 116
<212> TYPE: PRT
<213> ORGANISM: Homo sapiens

<400> SEQUENCE: 1

```
Leu Leu Glu Gln Ser Gly Ala Glu Val Lys Lys Pro Gly Ser Ser Val
1               5                   10                  15

Lys Val Ser Cys Lys Ala Ser Gly Asp His Tyr Gly Ile Asn Trp Val
            20                  25                  30

Arg Gln Ala Pro Gly Gln Gly Leu Glu Trp Met Gly Gly Ile Ile Pro
        35                  40                  45

Val Phe Gly Thr Thr Thr Tyr Ala Gln Lys Phe Gln Gly Arg Ala Thr
    50                  55                  60

Ile Thr Ala Asp Asp Ser Thr Gly Thr Ala Phe Leu Glu Leu Thr Arg
65              70                  75                  80

Leu Thr Phe Asp Asp Thr Ala Val Tyr Phe Cys Ala Thr Pro His Gln
            85                  90                  95

Leu His Val Leu Arg Gly Gly Lys Ala Leu Ser Pro Trp Asp Tyr Trp
        100                 105                 110

Gly Gln Gly Thr
        115

<210> SEQ ID NO 2
<211> LENGTH: 102
<212> TYPE: PRT
<213> ORGANISM: Homo sapiens

<400> SEQUENCE: 2

Met Ala Glu Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Arg Gly Gln Ala Pro Ser Leu Leu Ile
        35                  40                  45

Tyr Gly Thr Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65              70                  75                  80

Glu Asp Phe Ala Val Tyr Tyr Cys Gln Gln Tyr Asn Asp Trp Pro Ser
            85                  90                  95

Thr Phe Gly Gln Gly Thr
            100

<210> SEQ ID NO 3
<211> LENGTH: 348
<212> TYPE: DNA
<213> ORGANISM: Homo sapiens

<400> SEQUENCE: 3
ctgctcgagc agtcaggggc tgaggtgaag aagcctgggt cctcggtgaa ggtctcctgc      60
aaggcttctg gagaccacta tggtatcaac tgggtgcgac aggcccctgg acaagggctg     120
gagtggatgg gcggtatcat ccctgtcttt ggcacaacta cctacgcaca gaagttccag     180
ggcagagcca ccattaccgc ggacgactcc acgggacgg cctttttgga gctgaccaga      240
ctgacatttg acgacacggc cgtctatttc tgtgcgacac tcaccaact gcatgtcctc     300 cggggcggta agccctctc ccctgggac tactggggcc agggaacc                    348

<210> SEQ ID NO 4
<211> LENGTH: 306
<212> TYPE: DNA
<213> ORGANISM: Homo sapiens

<400> SEQUENCE: 4
```

-continued

```
atggccgagc tcacccagtc tccagccacc ctgtctgtgt ctccagggga aagagccacc     60
ctctcctgca gggccagtca gagtgttagc agtaacttag cctggtacca gcagaaacgt    120
ggccaggctc ccagtctcct catctacgga acatctacca gggccactgg tatcccagcc    180
aggttcagtg gcagtgggtc tgggacagag ttcactctca ccatcagcag cctgcagtct    240
gaagattttg cagtttatta ctgtcagcag tataatgatt ggccctccac cttcggccaa    300
gggaca                                                               306
```